(12) United States Patent
Von Oepen et al.

(10) Patent No.: US 12,318,288 B2
(45) Date of Patent: Jun. 3, 2025

(54) INSERT FOR DISTAL END CAP

(71) Applicants: Cephea Valve Technologies, Inc., San Jose, CA (US); EVALVE, INC., Santa Clara, CA (US)

(72) Inventors: Randolf Von Oepen, Aptos, CA (US); Timothy C. Reynolds, Sunnyvale, CA (US); Evelyn N. Haynes, Soquel, CA (US); Sean A McNiven, Menlo Park, CA (US); Dan Wallace, Santa Cruz, CA (US); Peter Gregg, Santa Cruz, CA (US); John Hill, San Jose, CA (US); David Tung, San Jose, CA (US)

(73) Assignees: Cephea Valve Technologies, Inc., Abbott Park, IL (US); EVALVE, INC., Santa Clara, CA (US)

( * ) Notice: Subject to any disclaimer, the term of this patent is extended or adjusted under 35 U.S.C. 154(b) by 1170 days.

(21) Appl. No.: 16/760,277

(22) PCT Filed: Oct. 30, 2018

(86) PCT No.: PCT/US2018/058258
§ 371 (c)(1),
(2) Date: Apr. 29, 2020

(87) PCT Pub. No.: WO2019/089627
PCT Pub. Date: May 9, 2019

(65) Prior Publication Data
US 2020/0323634 A1    Oct. 15, 2020

Related U.S. Application Data

(60) Provisional application No. 62/578,943, filed on Oct. 30, 2017.

(51) Int. Cl.
*A61F 2/24*     (2006.01)
*A61B 90/00*    (2016.01)

(52) U.S. Cl.
CPC ...... *A61F 2/2427* (2013.01); *A61B 2090/378* (2016.02); *A61F 2250/0098* (2013.01)

(58) Field of Classification Search
CPC ... A61F 2/24; A61F 2/011; A61F 2/82; A61B 25/00; A61B 25/098; A61B 25/0067; A61B 25/0108
See application file for complete search history.

(56) References Cited

U.S. PATENT DOCUMENTS

| 8,870,948 B1 | 10/2014 | Erzberger et al. |
| 10,368,990 B2 | 8/2019 | Noe et al. |

(Continued)

FOREIGN PATENT DOCUMENTS

| WO | 9533509 | 12/1995 | | |
| WO | WO-2015127283 A1 | * | 8/2015 | ........... A61F 2/2427 |

(Continued)

OTHER PUBLICATIONS

International Search Report for PCT/US18/58258 mailed Feb. 6, 2019; 4 pages.

*Primary Examiner* — Christopher D. Prone
(74) *Attorney, Agent, or Firm* — SLEMAN & LUND LLP

(57) ABSTRACT

An intravascular device delivery system has an elongated member, a guidewire receiving member, and a distal cap longitudinally fixed to a guidewire receiving member. The distal cap includes an insert having an elongate member, a rim member radially separated from the elongate member, and a wall member supporting the rim member, the wall member being disposed between the rim member and the elongate member.

18 Claims, 11 Drawing Sheets

(56) References Cited

U.S. PATENT DOCUMENTS

| | | |
|---|---|---|
| 2004/0127849 A1 | 7/2004 | Kantor |
| 2004/0133232 A1 | 7/2004 | Rosenbluth et al. |
| 2005/0038383 A1 | 2/2005 | Kelley et al. |
| 2005/0113804 A1* | 5/2005 | von Lehe ............... 604/528 |
| 2009/0036768 A1* | 2/2009 | Seehusen ............... A61L 29/18 |
| | | 604/529 |
| 2016/0158000 A1 | 6/2016 | Granada et al. |
| 2018/0028177 A1 | 2/2018 | van Oepen et al. |
| 2018/0092744 A1 | 4/2018 | von Oepen et al. |

FOREIGN PATENT DOCUMENTS

| | | |
|---|---|---|
| WO | 2016183523 A1 | 11/2016 |
| WO | 2016183526 A1 | 11/2016 |
| WO | 2017218877 A1 | 12/2017 |
| WO | 2018044449 | 3/2018 |
| WO | 2018094069 A1 | 5/2018 |

* cited by examiner

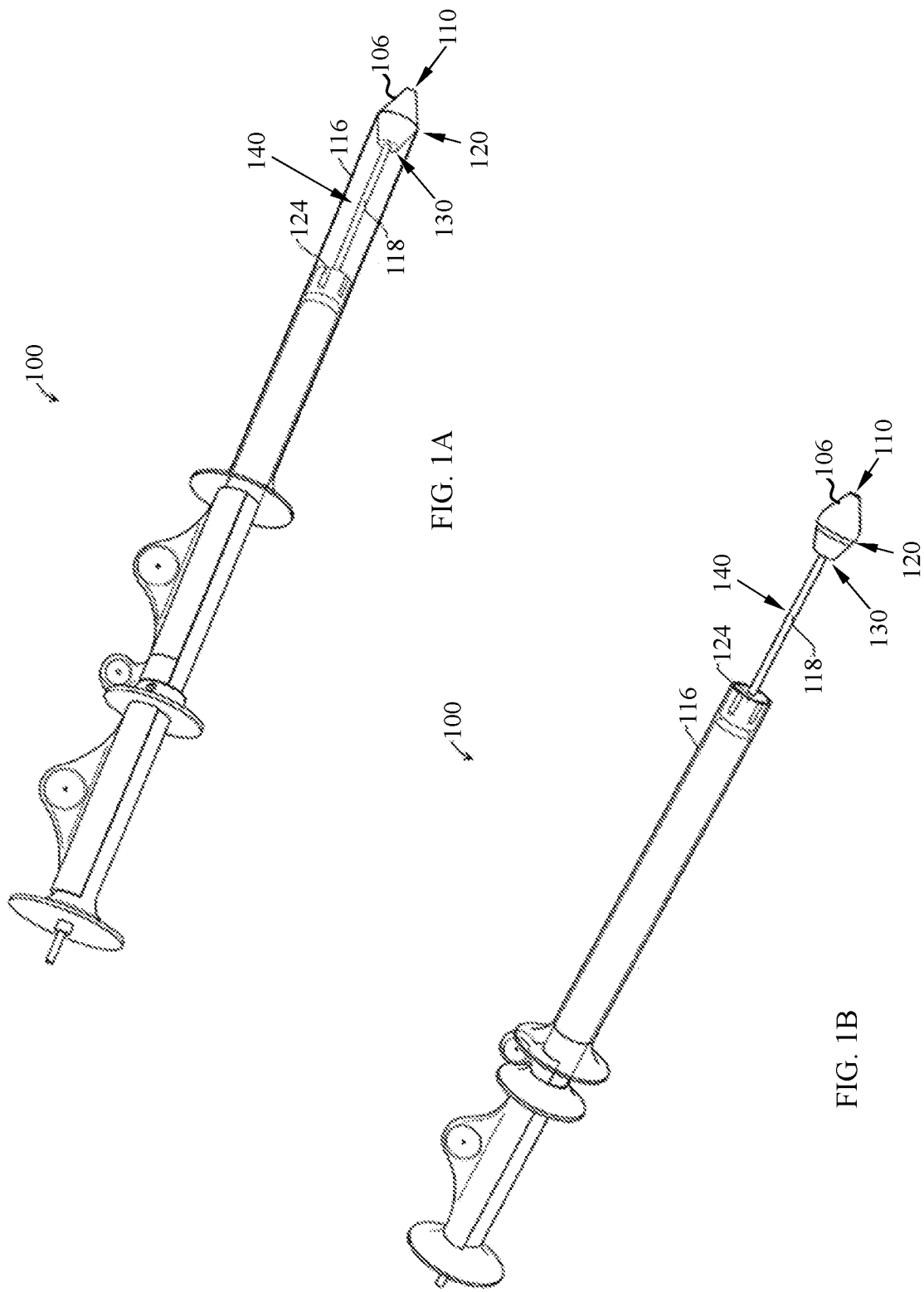

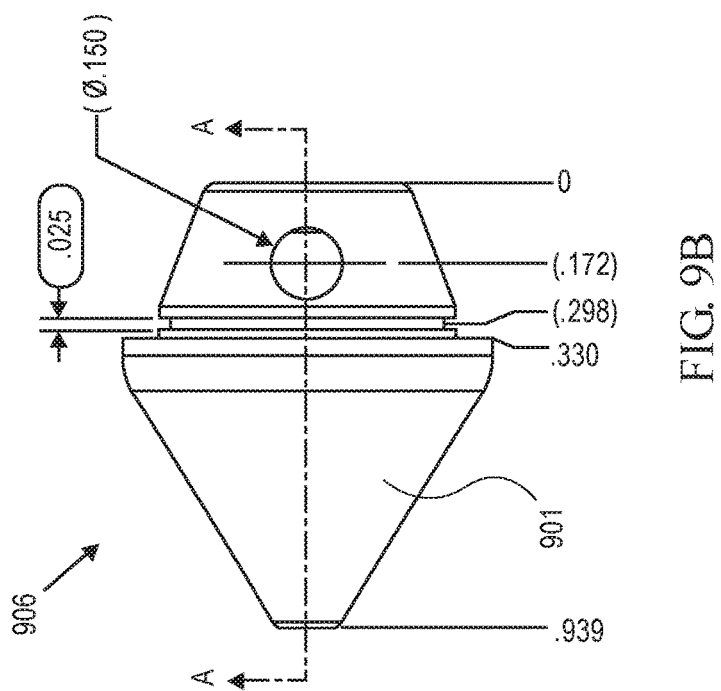
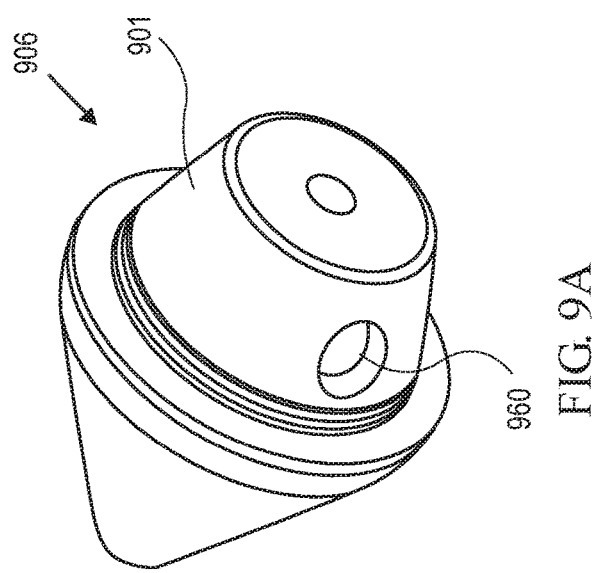
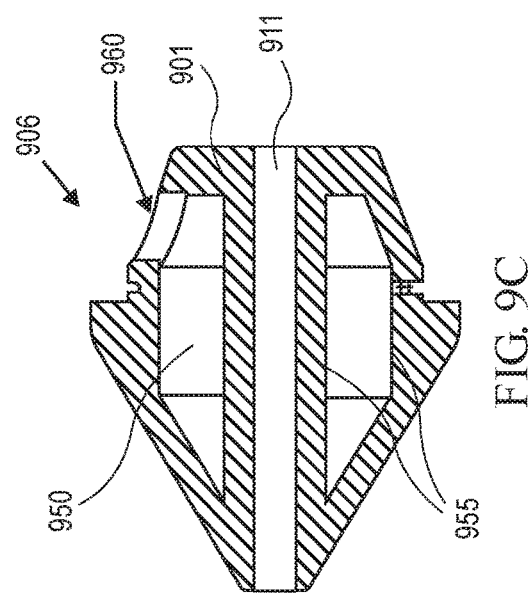

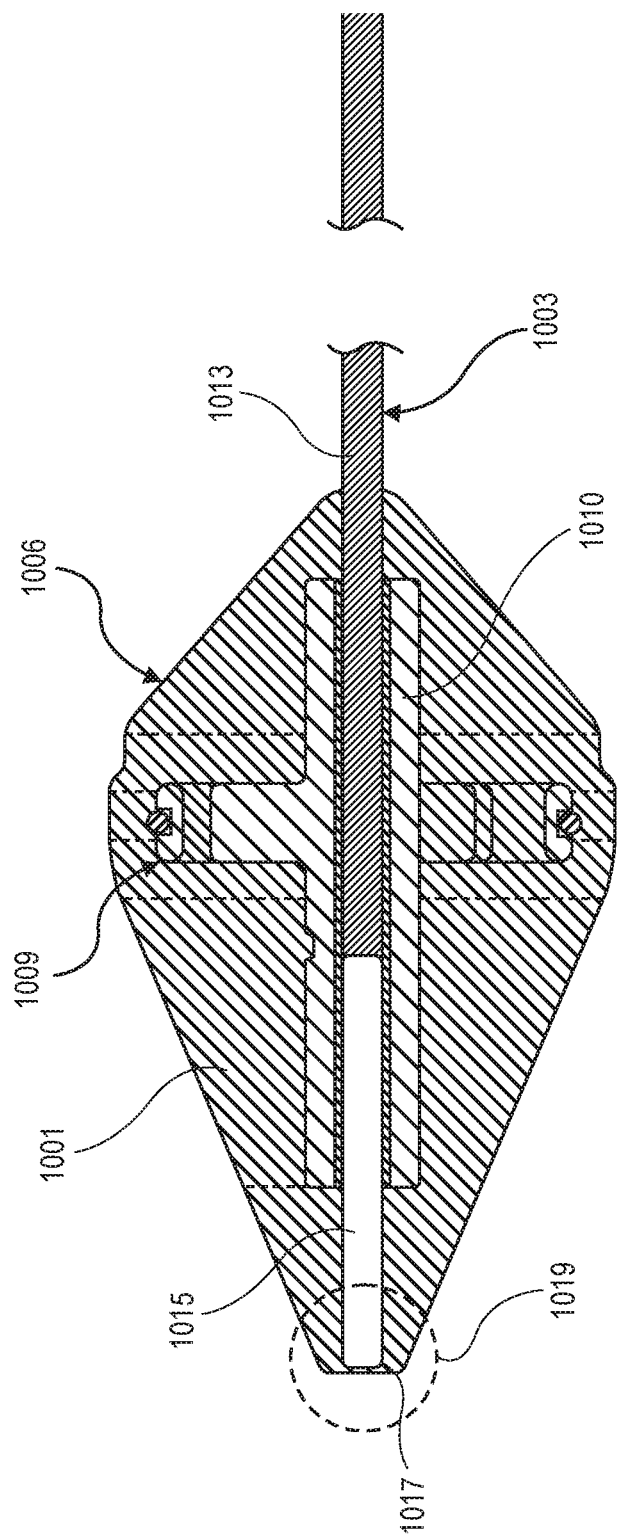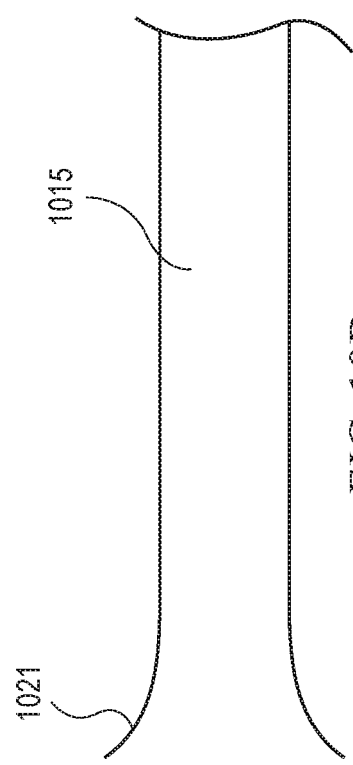
FIG. 10A
FIG. 10B

INSERT FOR DISTAL END CAP

CROSS-REFERENCE TO RELATED APPLICATION

This application is a national phase entry under 35 U.S.C. § 371 of International Application No. PCT/US2018/058258, filed Oct. 30, 2018, which claims priority from U.S. Provisional Application No. 62/578,943, filed Oct. 30, 2017, the entire disclosure of which is incorporated herein by reference.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The embodiments described herein relate to devices and systems used in medical procedures, such as intravascular procedures. In particular embodiments, the devices are configured to facilitate imaging of medical devices, or portions thereof, during medical procedures.

BACKGROUND

Cardiac valve replacement procedures involve replacing one or more valves in the heart with a replacement valve implant or a bioprosthesis. One of the most common types of valve replacements is a mitral valve replacement. The mitral valve lies between the left atrium and the left ventricle of the heart. Diseases such as degenerative mitral valve disease and mitral valve prolapse can cause mitral stenosis, in which the valve fails to open fully thereby obstructing blood flow and/or causing blood to flow passively in the wrong direction. If medical management and non-invasive treatments are unsuccessful, the mitral valve may need replacement.

Modern valve replacement techniques may involve minimally invasive procedures, which can be less traumatic and have less associated risks compared to open-heart procedures. The delivery devices used in minimally invasive replacement valve procedures generally have small profiles so that they can be inserted through the intravascular system to deliver the replacement valve in the appropriate area of the heart. Such minimally invasive procedures, are often performed with the aid of imaging techniques, where a doctor uses images of a patient's anatomy to guide the procedure. Such image-guided systems may use x-ray, ultrasound, or other imaging techniques to relay the patient's anatomy and movements of a medical device, such as a catheter, in relation to the patient. Imaging techniques can have certain limitations. For example, it may be difficult to determine an accurate position and orientation of a delivery device while in a patient's heart. For replacement valves, such positional information can be important for the valve to be installed in a correct position and orientation to ensure proper functioning of the replacement valve and to prevent injury to the patient. Devices and methods described herein can be used to address these and other issues.

SUMMARY OF THE DISCLOSURE

Described herein are devices and methods configured to facilitate imaging during medical procedures. In some embodiments, the devices are part of a larger device that is configured to perform one or more functions while in a patient's body. In particular embodiments, the devices are part of an implant delivery device that is configured to deliver an implant within a patient's body, such as a replacement heart valve.

In general, in one embodiment, an insert for a distal cap includes an elongate member comprising a lumen and a port, a rim member radially separated from the elongate member, and a wall member supporting the rim member. The wall member is disposed between the rim member and the elongate member.

This and other embodiments can include one or more of the following features. The rim member can include a circumferential groove configured to receive a radiopaque marker. The rim member can include a plurality of recesses. Each recess can be configured to receive a radiopaque marker. Collectively, the radiopaque markers in the plurality of recesses can approximate a ring. The lumen can include a plurality of mechanical engagement structures complementary to a plurality of mechanical engagement structures formed on a guidewire receiving member. The wall member can include a plurality of holes. The insert can further include a guidewire receiving member extending through the lumen of the elongate member. The guidewire receiving member can include a proximal section and a distal section, and the distal section can have greater flexibility than the proximal section. The proximal section and the distal section can be separate pieces adjoined to one another within the lumen of the elongate member.

In general, an intravascular device delivery system includes an elongated member with a proximal end, a distal end, and a longitudinal axis therebetween. The elongated member includes a guidewire receiving member extending from the proximal end to the distal end, and a distal cap longitudinally fixed to the guidewire receiving member. The distal cap includes an insert mounted to the guidewire receiving member and supporting a radiopaque marker.

This and other embodiments can include one or more of the following features. The distal cap can be over-molded with the insert. The insert can be adhesively bonded to the guidewire receiving member. The insert can include a plurality of spoke-like members extending between an elongate member and a rim member. Each of the plurality of spoke-like members can be tapered. The insert can include a plurality of through-holes extending along a longitudinal axis of the guidewire receiving member. The distal cap can include one or more echogenic features that allow visualization under echocardiography techniques. The one or more echogenic features can include pores of a porous material or one or more chambers within the distal cap. The guidewire receiving member can include a proximal section and a distal section, and the distal section can have greater flexibility than the proximal section. The proximal section and the distal section can be separate pieces adjoined to one another within the lumen of the elongate member.

In general, in one embodiment, an intravascular device delivery system includes an elongated member with a proximal end, a distal end, and a longitudinal axis therebetween, and a distal cap at a distal end of the elongated member. The elongated member is configured to hold a delivery device therein. The distal cap has an identification feature configured to be identified under x-ray or ultrasound.

This and other embodiments can include one or more of the following features. The identification feature can be radiopaque. The distal cap can include an insert supporting the radiopaque identification feature. The identification feature can be echogenic. The identification features can include porous or air-filled chambers within the distal cap. The distal cap can be tapered. The distal cap can include a blunt distal end. The identification can be a radial band extending around the distal cap.

In general, in one embodiment, a method of using an intravascular device delivery system includes: (1) positioning a radiopaque wire within the coronary sinus of a patient, the radiopaque wire enabling identification of a plane of the mitral annulus; (2) operating an intravascular device delivery system to cause a distal cap of the intravascular device delivery system to extend through the mitral annulus; and (3) positioning the distal cap to bring the radiopaque marker into planar alignment with the radiopaque wire, thereby bringing the distal cap into planar alignment with the plane of the mitral annulus. The intravascular device delivery system includes an elongated member with a proximal end, a distal end, and a longitudinal axis therebetween, a guidewire receiving member extending from the proximal end to the distal end, and a distal cap longitudinally fixed to the guidewire receiving member. The distal cap includes an insert mounted to the guidewire receiving member and supporting a radiopaque marker. The radiopaque marker has at least partially a band or ring structure.

This and other embodiments can include one or more of the following features. The method can further include delivery and/or deployment of an intravascular device at the mitral annulus following alignment of the distal cap to the plane of the mitral annulus. The distal cap can be overmolded with the insert. The insert can be adhesively bonded to the guidewire receiving member. The insert can include a plurality of spoke-like members extending between an elongate member and a rim member. Each of the plurality of spoke-like members can be tapered, and the insert can include a plurality of through-holes extending along a longitudinal axis of the guidewire receiving member. The method can further include positioning an imaging source relative to the patient such that the radiopaque wire positioned within the coronary sinus is substantially viewable as a line on resulting imagery. Positioning the distal cap to bring the radiopaque marker into planar alignment with the radiopaque wire can include positioning the radiopaque marker so as to be substantially viewable as a line on the resulting imagery.

In general, in one embodiment, a method of using an intravascular device delivery system, includes: (1) operating an intravascular device delivery system to cause a distal cap of the intravascular device delivery system to enter a patient's heart near the mitral annulus, the intravascular device delivery system including an elongated member and a distal cap longitudinally fixed to the elongated member, the distal cap includes one or more echogenic features; (2) determining a position of the distal cap relative to the mitral annulus by viewing the echogenic features using an echocardiography technique; and (3) positioning the distal cap relative to the mitral annulus based on the determined position.

This and other embodiments can include one or more of the following features. Aligning the distal cap relative to the mitral annulus can include: (1) adjusting a view of the delivery device within the patient to an en face view of the distal cap; and (2) aligning a center of the distal cap with respect to a center of the mitral annulus. Aligning the distal cap relative to the mitral annulus can include: (1) adjusting a view of the delivery device within the patient to a longitudinal view of the distal cap such that the left atrium and the left ventricle are visible, and (2) positioning the distal cap such that the distal cap is longitudinally aligned with one or more of the native valve annulus or leaflets. The method can further include identifying a plane of the mitral annulus using a radiopaque wire within the coronary sinus. Aligning the distal cap relative to the mitral annulus can further include using a radio-opaque marker of the distal cap to facilitate determination of an orientation of the distal cap with respect to the mitral annulus.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings.

FIGS. 1A and 1B show perspective views of an exemplary replacement valve delivery device.

FIG. 9A shows a perspective view of a distal cap having a cavity suitable for echocardiography visualization. FIG. 9B shows a side view of the distal cap shown in FIG. 9A.

FIG. 9C shows a section view A-A of the distal cap shown in FIG. 9B.

FIGS. 10A and 10B show an embodiment of a distal end cap with embedded insert and with a guidewire receiving member formed from separate sections each joined to the embedded insert.

DETAILED DESCRIPTION

Figure 2A:
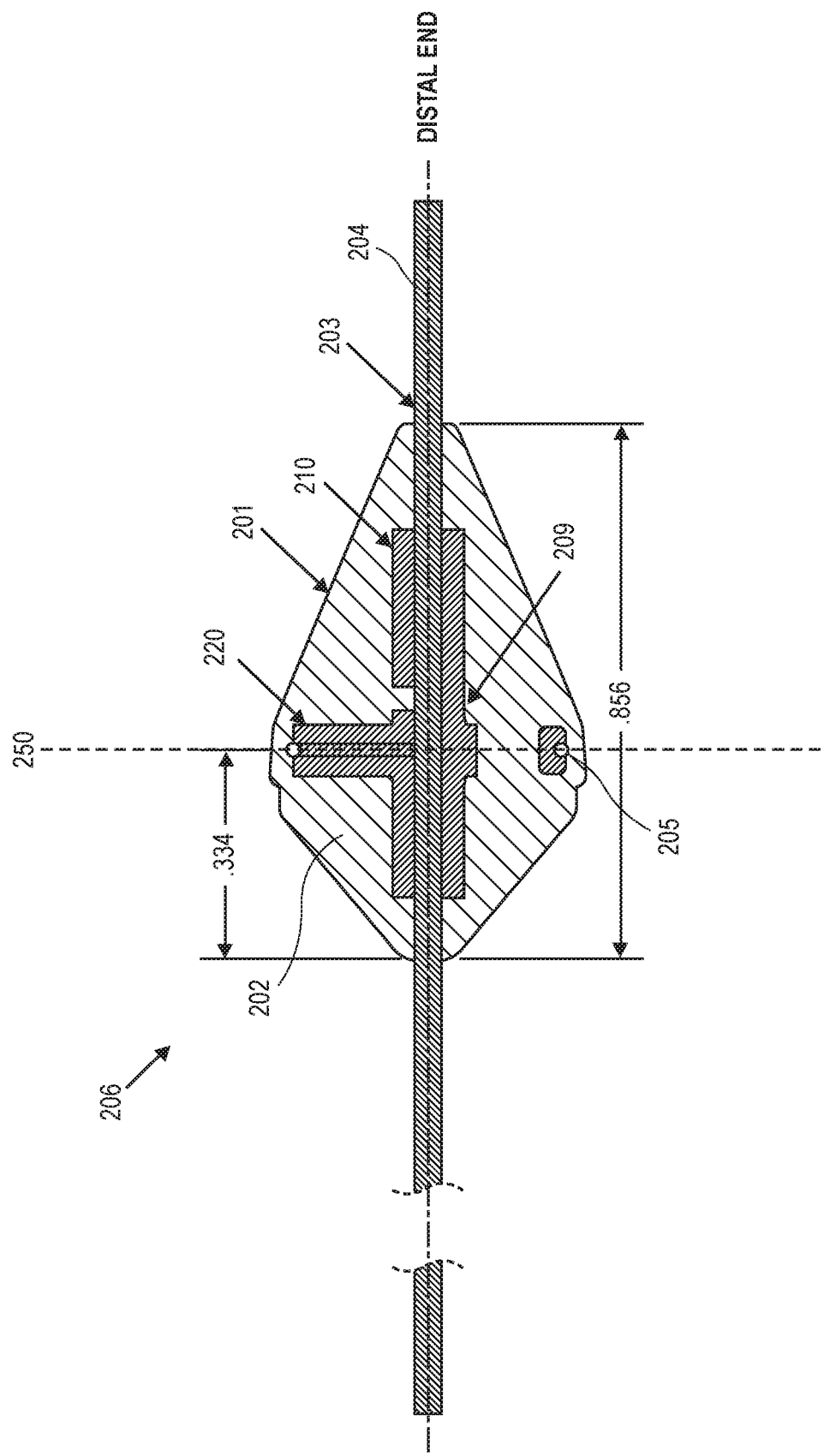
FIG. 2A shows a section view of a distal cap of a delivery device, the distal cap having an insert supporting a ring-shaped marker.

Described herein are devices and methods that can facilitate the delivery of one or more implants within patients. In some embodiments, the implant is delivered into a patient's vascular system. In some embodiments, the implant is a cardiac valve prosthesis, such as a replacement valve. Exemplary prosthetic valves described herein can include but are not limited to the expandable prosthetic valves described in U.S. Pat. No. 8,870,948, filed Jan. 31, 2014 and titled "SYSTEM AND METHOD FOR CARDIAC VALVE REPAIR AND REPLACEMENT," in International Patent Application No. PCT/US2016/032550, filed May 13, 2016 and titled "REPLACEMENT MITRAL VALVES," in U.S. patent application Ser. No. 14/677,320, filed Apr. 2, 2015 and titled "REPLACEMENT CARDIAC VALVES AND METHODS OF USE AND MANUFACTURE," and U.S. patent application Ser. No. 16/012,666, filed Jun. 19, 2018 and titled "REPLACEMENT MITRAL VALVES," each of which is incorporated herein by reference in its entirety.

The devices described herein can be part of a larger delivery device or system that is configured to deliver an implant into a patient. For example, the devices can be part of a cardiac replacement valve delivery device that is designed to deliver a replacement valve through a surgical route (e.g., during a cardiopulmonary bypass) or through a trans-septal, atrial, or trans-atrial route (e.g., by making a small incision in the patient's body and passing the prosthesis through the apex of the heart to, for example, the mitral valve). Such a delivery device could also be utilized in a transcatheter aortic valve replacement (TAVR) procedure. Exemplary delivery devices and systems described herein can include but are not limited to those described in International Patent Application No. PCT/US2017/062045, filed Nov. 16, 2017 and titled "CARDIAC VALVE DELIVERY DEVICES AND SYSTEMS," in International Patent Application No. PCT/US2016/032546, filed May 13, 2016 and titled "CARDIAC VALVE DELIVERY DEVICES AND SYSTEMS," International Patent Application No. PCT/US2017/037850, filed Jun. 16, 2017 and titled "CARDIAC VALVE DELIVERY DEVICES AND SYSTEMS," United States Patent Application No. 2018/0028177A1, filed Jul. 27, 2017 and titled "SYSTEMS AND METHODS FOR DELIVERING AN INTRAVASCULAR DEVICE TO THE MITRAL ANNULUS," and United States Patent Application No. 2018/0092744A1, filed Oct. 4, 2017 and titled "SYSTEMS AND METHODS FOR DELIVERING AND DEPLOYING AN ARTIFICIAL HEART VALVE WITHIN THE MITRAL ANNULUS," each of which is incorporated herein by reference in its entirety.

FIGS. 1A and 1B illustrate an exemplary delivery device 100 that is configured to deliver an intravascular device within a patient's body. The delivery device 100, in particular, is configured to deliver and deploy a self-expanding mitral valve prosthesis, e.g., through a trans-atrial delivery method. The delivery device 100 can allow self-expansion of a distal portion of the valve prosthesis and controlled deployment of a proximal portion of the valve prosthesis. The delivery device 100 can include a sheath 116 with a central stem 118 disposed therein. The central stem 118 can have a distal region that is coupled to a distal cap 106 (also referred to as a nosecone or tip). A valve region 140 proximal to the distal cap 106 can be sized and shaped to hold the valve prosthesis. The sheath 116 can be configured to fully extend over the central stem 118, as shown in FIG. 1A, such that the valve prosthesis is enclosed within the sheath 116. Constraints 124 may be used to maintain the valve prosthesis in a collapsed configuration when the valve prosthesis is within the sheath 116. The sheath 116 can also be configured to be proximally withdrawn relative to the central stem 118, such as shown in FIG. 1B. When the sheath 116 is withdrawn, the distal end of the valve prosthesis, e.g., distal anchor, can be allowed to self-expand and deploy within the patient's body. In some embodiments, the delivery device 100 includes a button or knob (e.g., rotating knob) that controls movements of the sheath 116.

The distal cap 106 can be positioned at the distal end of the delivery device 100 and can be configured to aid with inserting the delivery device 100 into a position within a patient's heart for successful valve placement. In some cases, the tapered shape of the distal tip 110 can provide a smooth taper for insertion or passing through tissue. In some cases, the tapered shape of the distal tip 110 can provide a smooth transition over the guidewire (if used). In some cases, the distal cap 106 has a tapered distal tip 110 to provide a small surface area such that if the distal cap 106 touches a portion of the patient's heart, less damage will be done to the heart. The distal tip 110 of the distal cap 106 can also be rounded or blunt so as to decrease the risk of puncturing the patient's heart if the distal tip 110 contacts the surface of the heart. In some embodiments, the distal cap 106 has a bullet-like contour. The distal cap 106 can include a sheath contact region 120 that is configured to engage with and cooperate with the sheath 116 to enclose the valve prosthesis within the sheath 116 (e.g., before being deployed). For example, the knob of the delivery device 100 can be used to extend the sheath 116 until it meets up with the sheath contact region 120. In some cases, the sheath contact region 120 has a larger diameter than adjacent portions (e.g., distal tip 110 and proximal portion 130) of the distal cap 106. In some embodiments, the proximal portion 130 of the distal cap 106 is coupled with the central stem 118 and can also have a tapered shape. Delivery devices described herein can vary with respect to their various features and modes of delivering the valve prosthesis and are not limited to those shown and described in FIGS. 1A and 1B. For example, the delivery devices can include more than one sheath and/or include various valve constraint structures and configurations.

The delivery devices described herein can include various features to help guide the delivery device while in the patient. For example, radio-opaque markers in or on the delivery device can enable a physician to view the location of the delivery device (or a portion thereof) using an imaging device, x-ray, ultrasound, echocardiography, fluoroscopy, and/or other imaging techniques to ensure proper positioning of the implant within the patient. The markers can be positioned in or on one or more locations of the delivery device. For example, returning to FIGS. 1A and 1B, a marker may be positioned in or on the distal cap 106. In some cases, the marker can be in or on the sheath 116. In some cases, the marker can be in or on a valve cover used to cover the replacement valve. In some cases, the marker can be in or on the central stem 118. In some embodiments, the marker can be in or on a structure used to push the replacement valve from the sheath 116.

With many medical devices, including temporarily or permanently implanted devices, it is often desirable to reduce the device profile. Even if a radio-opaque marker can be made relatively thin, it nevertheless could increase the profile of the device if placed on an outside diameter. As an example, if a marker is placed on the outside of the sheath 116, it may increase the diameter of the sheath 116. On the other hand, if the marker is placed on the inside of the sheath 116, it might interfere with the replacement valve contained therein, such as when the sheath 116 is moved relative to the replacement valve (e.g., pulled back or pushed forward). Placing a marker on the central stem 118 might position it too far from the distal end of the replacement valve. A marker on a distal end of a structure used to advance the replacement valve might be difficult to see, depending on the material forming the marker. Based upon this, in some configurations, the marker may be placed in the end of the distal end of the delivery device, such as within the distal cap 106.

Figure 2B:
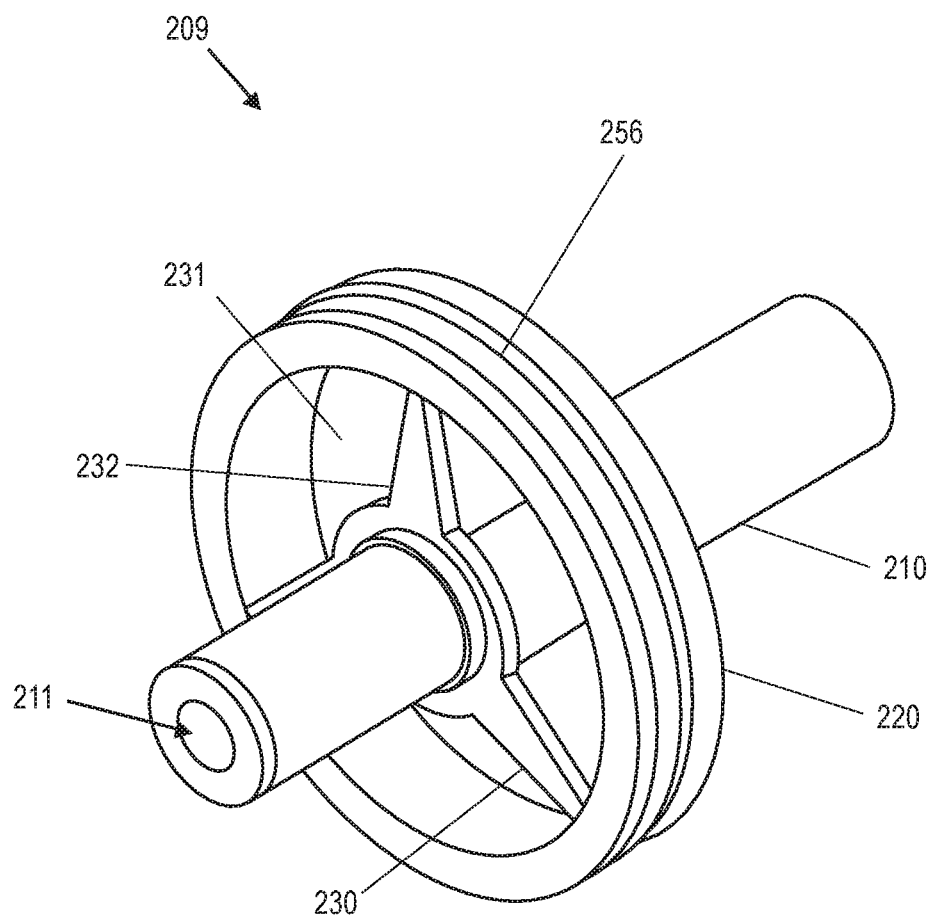
FIG. 2B shows a perspective view of the insert of FIG. 2A.
Figure 3B:
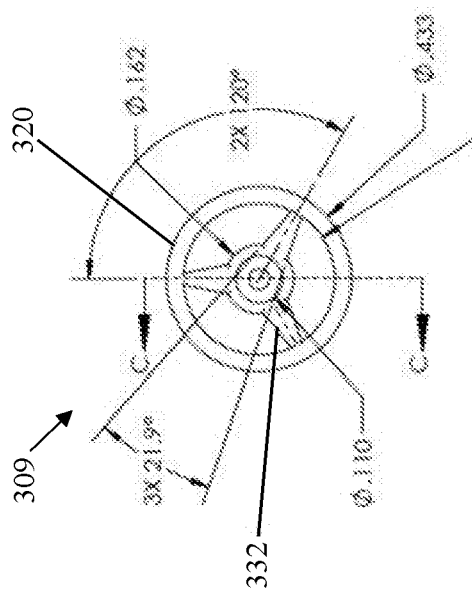
FIGS. 3A-3D show various views of an insert for supporting a ring-shaped marker.
Figure 3D:
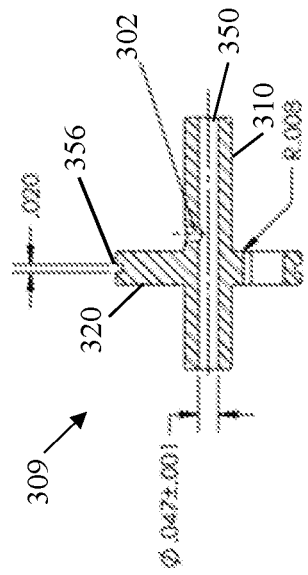
Figure 3A:
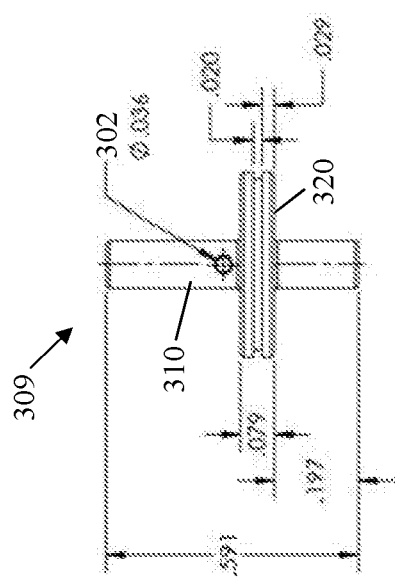
Figure 3C:
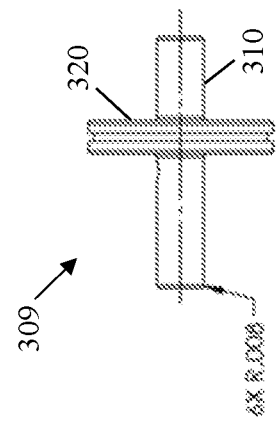

FIG. 2A shows a section view of an exemplary distal cap 206 with an insert 209 embedded therein. FIG. 2B shows a perspective view of the insert 209 alone. The distal cap 206 can included a molded portion 201, which can encase a least a portion of the insert 209. In some cases, the molded portion 201 fully encases an outer surface of the insert 209. The molded portion 201 can be made from material 202 suitably flexible to allow an atraumatic navigation of the distal cap 206 through the anatomy of the patient. In some embodiments, the molded portion 201 is made of a soft polymer, silicon and/or rubber. In some cases, the molded portion 201 can be made of a foamy material to allow visualization under echocardiography guidance. In some cases, a contrast agent like barium sulfate could be added to the material 202 of molded portion 201 to allow a ghost-like image visualization of the distal cap 206 under x-ray.

The insert 209 can include an elongate member 210 and a rim member 220 (also referred to as a rim). The rim 220 can be radially separated from the elongate member 210, and may be supported by and connected to the elongate member 210 by a wall member 230 (also referred to as a wall). A perimeter of the rim 220 can include a groove 256 that is configured to receive a marker 205. The marker 205 can be made of a radio-opaque material such that the marker 205 can be visible using any of a number of imaging techniques. In some embodiments, the marker 205 is in the form of a band, wire, or other elongate structure. The insert 206 can be embedded within the distal cap 206 such that a plane 250 defined by the rim 220 is (e.g., substantially) perpendicular with respect to a longitudinal axis 204 of the distal cap 206.

In some embodiments, the wall 230 of the insert 206 has a spoke-like configuration with a plurality of spokes 232 separated by openings 231 (e.g., through-holes). The openings 231 between the spokes 232 may provide access for receiving the material 202 of the molded portion 201 of the distal cap 206. The openings 231, in some configurations, can aid with the flow of the polymer or other material during molding. In some cases, the width of the spokes 232 can taper from the elongate member 210 toward the rim 220. Alternatively, the width of the spokes 232 may taper in the opposite direction (i.e., from the rim 220 toward the elongate member 210). In addition, the spokes 232 may have a uniform thickness or can taper in a direction transverse to the longitudinal axis 204 so that the spokes 232 are thicker closer to the elongate member 210 versus at the rim 220. The reverse is also possible. In other embodiments, the wall 230 is a solid piece (e.g., having no spokes and openings).

The distal cap 206 can be coupled with a guidewire receiving member 203, which can have a central lumen that is configured to receive a guidewire for guiding the delivery device within the patient's body. The guidewire receiving member 203 may correspond to or be part of a central stem of the delivery device. Generally, the guidewire receiving member 203 should be strongly coupled with the distal cap 206 to prevent the distal cap 206 from being sheared from the guidewire receiving member 203 while in the patient's body. In some cases, a simple over-mold or gluing of the molded portion 201 to the guidewire receiving member 203 may not provide a strong enough connection, depending on the material choice of the guidewire receiving member 203 and the material 202 of the molded portion 201. To overcome this potential difficulty, the distal cap 206 can be secured to the guidewire receiving member 203 through a mechanical interaction. For example, elongate member 210 of the insert 209 can be configured to engage with the guidewire receiving member 203. The guidewire receiving member 203 can be configured to fit within a lumen 211 of the longitudinal axis 204 of the distal cap 206. This can provide extra mechanical engagement between the distal cap 206 and the guidewire receiving member 203 (e.g., beyond the molding over of molded portion 201 over the guidewire receiving member 203) to prevent separation of distal cap 206 from guidewire receiving member 203. In some cases, the insert 209 can be adhesively affixed to the guidewire receiving member 203.

In some cases, the insert 209 is separately manufactured prior to attachment to the guidewire receiving member 203. For example, the insert 209 can be manufactured using machining, injection molding, additive manufacturing (e.g., three-dimensional printing), other manufacturing technique or any combination thereof. The insert 209, or portions thereof, can be made from any of a variety of materials including but not limited to polymers, metal, ceramics, composites, alloys and/or any combination thereof. Material for the insert 209, in some configurations, could be a polycarbonate and/or a nylon material since these materials may be injection moldable and may be easily glued with variety of different adhesives.

As described above, the insert 209 may be adhesively affixed to the guidewire receiving member 203. In some cases, the elongate member 210 includes a port through which glue or an adhesive can be ejected to aid with bonding or connecting the insert 209 to the guidewire receiving member 203.

FIGS. 3A-3D show various views of an insert 309 having a port 302 configured to accept adhesive injected therethrough for bonding the insert 309 to a guidewire receiving member. The port 302 may correspond to a through-hole within at least one of the walls of the elongate member 310 that provides access to the lumen 350 of the elongate member 310. In some embodiments, the port 302 is positioned in a longitudinally central region of the elongate member 310 (e.g., near the rim 320). Various glues or adhesives are known to those skilled in the art, including, but not limited to UV and non-UV curable adhesives. In other configurations, whether in addition to or instead of using adhesives, the elongate member includes a plurality of mechanical engagement structures to interference or friction fit with the outside of the guidewire receiving members. For instance, complementary dentents, grooves, undercuts or other engaging structures may allow the insert to be securely attached to the guidewire receiving member before molding. In some embodiments, the insert has a plurality of ports (holes). Note that FIGS. 3A-3D show various exemplary dimensions of the port 302, elongate member 310, rim 320, spokes 332 and groove 356. These dimensions are shown as examples only and are not intended to limit the scope of dimensions of an insert in accordance with embodiments described herein.

Returning to FIGS. 2A and 2B, the radio-opaque marker 205 can be placed in the groove 256 of the insert 209, and optionally attached using adhesives or mechanical engagement. In some embodiments, the marker 205 is placed after the insert 209 has been connected to the guidewire receiving member 203. In other embodiments, the marker 205 is placed before or during the coupling to the insert 209 to the guidewire receiving member 203. With the marker 205 in place, the guidewire receiving member 203 with the insert 209 attached, can be placed into a mold and over-molded with material 202 of molded portion 201, such as a polymer described above, to form the distal cap 206. The open structure of the insert 209 attached to the guidewire receiving member 203 may allow for a strong mechanical interaction of the distal cap 206 with the insert 209. The groove 256 in the insert 209 may allow the marker 205 to be positioned perpendicularly to the axis of the guidewire receiving member 203, as described above. After the distal cap 206 is formed, the distal cap 206 may be assembled into a delivery device, such as delivery device 100 shown in FIGS. 1A and 1B.

Figure 4B:
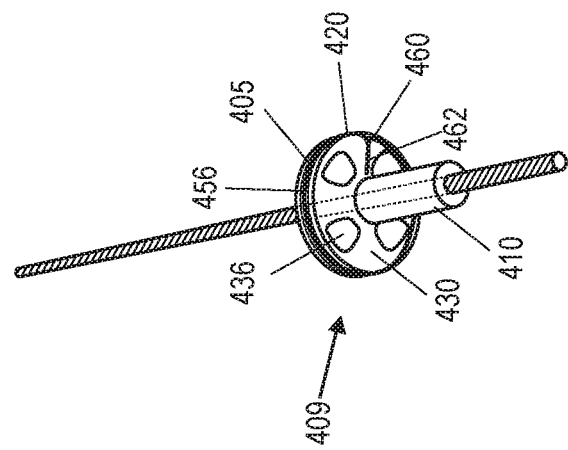
FIGS. 4A and 4B show perspective views of inserts having ring-shaped markers.
Figure 4A:
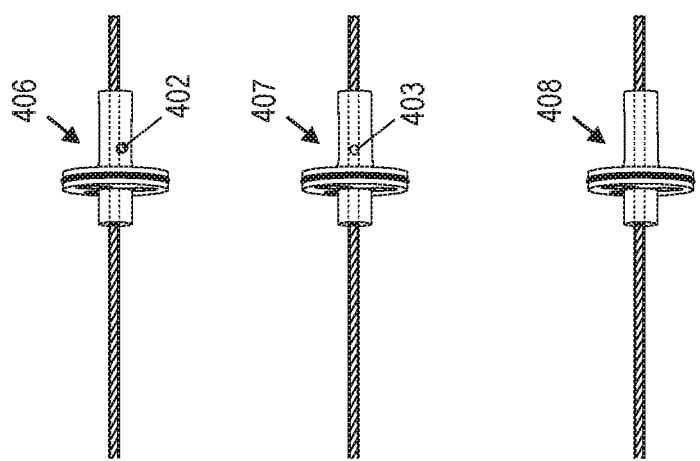

FIGS. 4A and 4B show inserts 406, 407, 408, 409 according to an alternative exemplary embodiment. Inserts 406, 407, 408, 409 can include a wall 430 connecting the rim 420 to the elongate member 410 that includes circular holes 436. This can be an alternative to a spoke-like structure. The holes within the wall are not limited to circular shapes. For example, the holes can have polygonal (e.g., triangular, square, rectangular, hexagonal, etc.) shapes. The ports 402, 403 can provide access to the lumen of the elongate member 410 for injection of an adhesive for bonding with a guidewire receiving member, as described herein. The rim 420 can have a groove 456 configured to accept a band-shaped marker 405. Alternatively, instead of a single groove, the rim 420 can include a plurality of recesses, with each recess receiving a radio-opaque marker. The multiple grooves can be positioned along different lengths of the elongate member 410 and/or at different radial distances from the elongate member 410. The combination of those recess and markers may approximate a ring or a plurality of rings. In still another configuration, the groove 456 can include a plurality of recesses with the marker extending across the recesses, with those recesses optionally filled with additional radio-opaque material, or some other material. In alternate configurations, the marker can include a plurality of discrete radio-opaque or radiopaque elements that can general approximate a ring or portion of a ring.

The marker 405 can optionally can include an elongate end 460 that is mounted through a base of the groove and into the wall 430 of the insert 409. For instance, the wall 430 can include an access route 460 through which one or more an elongate ends 462 of the marker 405 can enter the wall 430 towards the elongate member 410 (e.g. transverse direction). This configuration may help to further secure the marker 405 to the insert 409 by providing additional mechanical engagement between the marker 405 and the insert 409. In some cases, the access route 460 includes a hole or groove through which the elongate end 462 can be inserted. Alternatively or additionally, an adhesive can be used to couple the marker 405 with the wall 430. For example, an adhesive can be injected within the groove of the rim 420 and/or within the access route 460 before positioning the marker 405 therein.

As described above, the devices described herein can be used to visualize a position the delivery device while in a patient during a medical procedure. For example, the devices can be used to ensure that the delivery device is positioned correctly when repairing the heart or placing an intravascular device, such as a valve prosthesis. One or more of the distal cap embodiments described herein may be utilized in an interventional cardiac procedure. One exemplary embodiment includes the steps of: positioning a radio-opaque guidewire within the coronary sinus of a patient, the radio-opaque guidewire enabling identification of a plane of the mitral annulus; operating an intravascular device delivery system to cause a distal cap to extend through the mitral annulus, the distal cap including a radio-opaque marker band at least partially formed in a ring structure; positioning the distal cap to bring the radiopaque marker band into planar alignment with the radio-opaque guidewire, thereby bringing the distal cap into planar alignment with the plane of the mitral annulus. Such a procedure may facilitate proper positioning of the replacement valve since in the human anatomy the coronary sinus is typically not completely in one plane.

Figure 5:
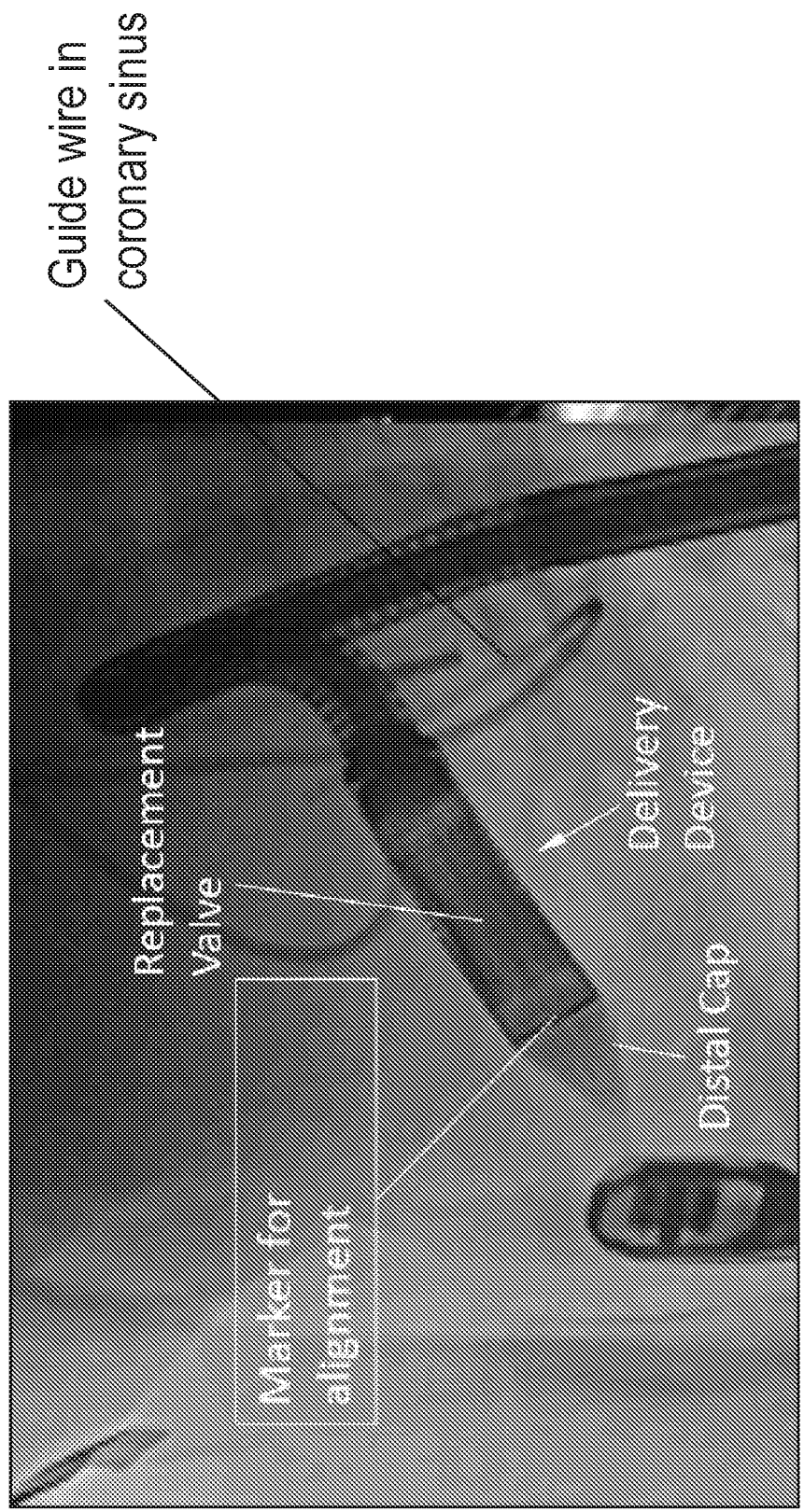
FIG. 5 shows an image of a delivery device with a distal cap having a ring-shaped marker in a patient's body.
Figure 6:
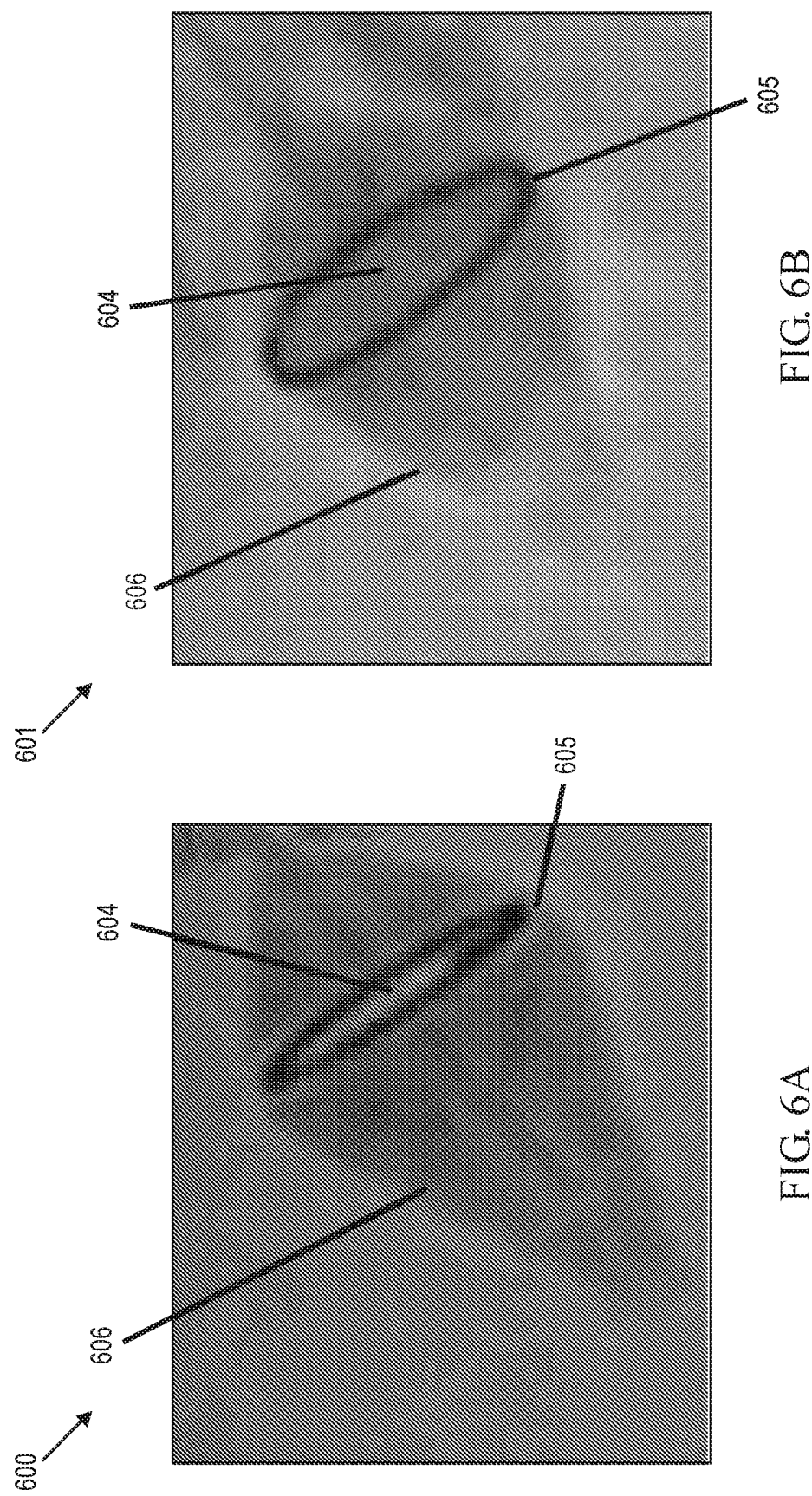
FIGS. 6A and 6B show images of the delivery device with a distal cap having a ring-shaped marker used to align the delivery device in a patient's body.

FIGS. 5-6B illustrate various steps of positioning a replacement valve into the mitral annulus in accordance with some embodiments. FIG. 5 shows an image of a delivery device with a replacement valve loaded therein being inserted into a patient's heart. During such a procedure, a guidewire can be placed into, for example, the coronary sinus which runs parallel to the mitral annulus. The guidewire may be made of a radio opaque material so that it is visible under x-ray, or other imaging technique, allowing the physician or operator to identify, for example, the plane of the mitral annulus. For instance, the physician or operator can position the imaging source (e.g., using a C-arm of an x-ray machine) in an orientation so that sections of the radio-opaque guidewire positioned within the coronary sinus overlap and are substantially viewable as a line in the corresponding two-dimensional image. In other words, the imaging source can be positioned such that the x-rays (or ultrasound or other source suitable for the particular imaging technique used) pass through the patient in a path substantially parallel to the plane of the mitral annulus.

FIGS. 6A and 6B show images of the delivery device after the imaging source has been oriented to view the delivery device in a substantially parallel direction with respect to the plane of the mitral annulus. The ring-shaped marker 605 of the distal cap 606 of the delivery device can be used to determine the orientation of the delivery device, and the replacement valve loaded therein, with respect to the mitral annulus. For example, the position of the delivery device can be manipulated to move the orientation of the ring-shaped marker 605 from a first position 601 to a second position 600 (or vice versa). Features of the ring-shaped marker 605 can be used to determine its orientation with respect to the imaging source and the mitral annulus. For instance, the delivery device can be moved such that opposing sides of the ring-shaped marker 605 overlap and are viewable as substantially a line as viewed from the perspective of the imaging device, which orientation that was already established with the guidewire. For example, the sides of the ring-shaped marker 605 at the second position 600 can be viewed as more aligned (overlapping) with each other compared to at the first position 601, indicating a plane of the marker 605 may be more perpendicular with respect to the imaging device in the second position 600. As illustrated, the orientation of the ring-shaped marker 605 can also be identified by the extent to which an opening 604 of the marker 605 is visible. For instance, the opening 604 of the marker 605 at the second position 600 is smaller than at the first position 601, indicating a plane of the marker 605 may be more perpendicular with respect to the imaging device at the second position 600 compared to first position 601. In this manner, the more aligned the distal cap 606 is to the mitral annulus, the more line-like the two-dimensional visualization of the radio-opaque marker band 605 may appear. Likewise, the less aligned the distal cap 606 is to the mitral annulus, the less line-like (and more band-like or ring-like) the two-dimensional visualization of the radio-opaque marker band 605 may appear. In these ways, features of the marker 605 can be used to provide orientation information during the medical procedure.

Once it is determined that the ring-shaped marker 605 is substantially perpendicular with respect to the imaging device (and thus substantially parallel with respect to the plane of the mitral annulus), the delivery device can be used to deliver (deploy) the replacement valve within the mitral annulus. In some cases, the ring-shaped marker 605 is further used to identify the position and orientation of the delivery device during deployment of the replacement valve and/or during removal of the delivery device from the patient's heart.

Figure 7:
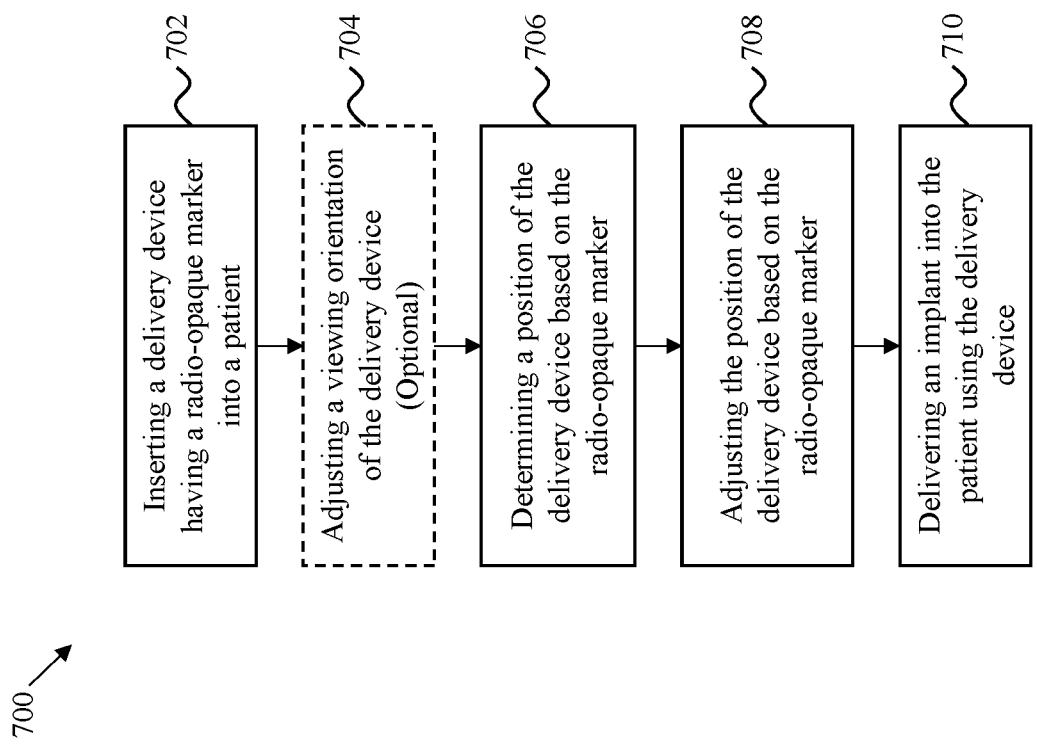
FIG. 7 shows a flowchart indicating a process for using a radio-opaque marker to adjust a deliver device in a correct orientation within a patient's body.

FIG. 7 shows a flowchart 700 indicating a process for using a delivery device having a radio-opaque marker during a medical procedure, in accordance with some embodiments. At 702, the delivery device is inserted into a patient and moved to a location at or near a target site for delivering the implant. In some cases, the delivery device can be configured to deliver an implant, such as a replacement valve or other intravascular implant. The delivery device can be inserted, for example, via a surgical route or a minimally invasive route (e.g., via small incision of the vascular system). The delivery device may include, or be used in conjunction with, a catheter and/or guidewire to facilitate the guiding of the delivery device to the target site. The radio-opaque marker can be in or on any of a number of locations of the delivery device, such as the distal cap and/or other locations described herein.

At 704, one or more features of the delivery device, or an associated device, can optionally be used to adjust an orientation of a imaging source with respect to the delivery device. For example, the imaging source may be adjusted such that sections of a radio-opaque guidewire (e.g., within the coronary sinus) align or overlap (e.g., from substantially a line) from the perspective of the viewing source. Such alignment can be used to infer the orientation of the delivery device with respect to the target site (e.g., the mitral annulus). At 706, the radio-opaque marker can be used to determine a three-dimensional position or orientation with respect to the target site. For example, the position of one or more features of the radio-opaque marker as viewed from the perspective of the imaging source can be used determine whether the delivery device is in a correct orientation with respect to the target site. In the case of a ring-shaped marker, the features may correspond to opposing sides of the ring.

At 708, a position of the deliver device, or a portion thereof, can be adjusted to place the delivery device in the correct orientation at the target site based on the orientation of the radio-opaque marker. For example, the position of the delivery device can be adjusted such that alignment features of the radio-opaque marker are aligned from the perspective of the imaging source. In the case of a ring-shaped marker, the delivery device can be manipulated such that opposing sides of the ring align or overlap (e.g., from substantially a line). That is, the ring-shaped marker can define plane as a basis for adjusting the delivery device in the correct orientation at the target site. In this way, the radio-opaque marker can be used to place the delivery device, and the implant, in the correct orientation with respect to the target site (e.g., mitral annulus). At 710, the delivery device can be used to deliver the implant (e.g., replacement valve) into the patient. The delivery device may then be removed from the patient.

As described above, in some embodiments, the distal cap can include one or more echogenic features that allow visualization, or improved visualization, under echocardiography techniques. The echogenic features can include one or more cavities, such as pores of a porous material or chambers, within the distal cap. Ultrasound incident on the distal cap can bounce off the walls that define the cavities such that an ultrasound imaging device can detect the reflecting sound waves. In this way, the distal cap can be configured to be visualized, or more easily visualized, using an ultrasound imaging device. The echogenic feature(s) may be used in addition to or instead of radio-opaque marker(s) for visualizing the position of the distal cap when in a patient's body, as described herein.

Figure 8:
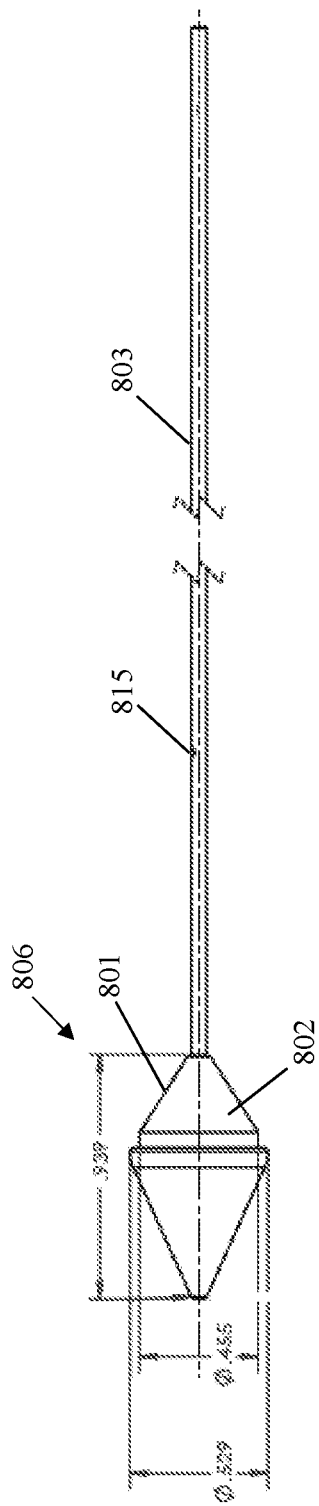
FIG. 8 shows a side view of a distal cap assembly formed with porous material for echocardiography visualization.

In some embodiments, the echogenic features correspond to pores within a foamy (e.g., porous) material that make up at least a portion of the distal cap. In some cases, the foamy material is formed by injecting a foaming agent into or with a plastic material during molding of the distal cap to the guidewire receiving member. To illustrate, FIG. 8 shows an exemplary distal cap 806 and guidewire receiving member 803. A molded portion 801 of the distal cap 806 can be molded over the guidewire receiving member 803 to form a bond therebetween. The molded portion 801 can be formed of a molded material 802 (e.g., plastic) that can be co-injected with a foaming agent. Examples of foaming agents can include chemical foaming agents such as Foamazol™ or other products provided by Bergen International LLC based in New Jersey, U.S.A. In some cases, a solid plastic injection stage begins a split second before the foamed plastic stage causing the foamed plastic to move to the inside of the solid material, such that the molded portion 801 has a solid skin with a foamed core. In some embodiments, an insert and/or a radio-opaque marker is/are molded within the molded portion 801, as described herein. In some embodiments, the molded portion 801 does not include an insert and/or a radio-opaque marker therein. In some cases, an exterior surface of the molded portion 801 appears smooth as the porous aspects are internal to the molded portion 801. The guidewire receiving member 803 can include a through-hole 815 to enable flushing of the delivery device or replacement valve at targeted locations through the guidewire receiving member 803. Note that the dimensions shown FIG. 8 are provided as examples only and are not intended to limit the scope of dimensions of a distal cap assembly in accordance with embodiments described herein.

In some embodiments, the echogenic features correspond to one or more pockets (also referred to as chambers) within the distal cap. FIGS. 9A-9C show various views of a molded portion 901 of a distal cap 906 having an internal air pocket 950. The air pocket 950 defines walls 955 internal to the molded portion 901 that can reflect sound waves for sufficient for echogenicity and ultrasonic detection using an ultrasonic imaging device. In some embodiments, the air pocket 950 may be formed using an additive manufacturing process. In some embodiments, the air pocket 950 may be formed by injection molding around an insert material having a corresponding shape as the air pocket 950. After the molded material 901 is sufficiently hardened, the insert material can be removed (for example, via opening 960) such that the pocket 950 are hollow. In some cases, the opening 960 is filled after the insert material is removed. In some embodiments, the air pocket 950 can have a band shape that encircles a central lumen 911 of the molded portion 901. In other embodiments, the molded portion includes multiple air pockets that can cooperate to provide a band or other shape within the molded portion. Note that the dimensions shown FIG. 9B are provided as examples only and are not intended to limit the scope of dimensions of a distal cap in accordance with embodiments described herein.

The echogenic features described herein can help with determining a depth and/or centrality of the distal cap (e.g., 806 or 906) and thus the overall delivery system. In one embodiment, in an end face view of the distal cap, looking at the mitral annulus, the echogenic distal cap can be visible as a bright spot or form depending on the angle of view. In contrast, the mitral annulus may be visible as a shadowy form, identifiable via shape and motion, for example, in a standard echocardiogram or in three-dimensional echocardiogram. Using this view, the distal cap (and thus the delivery device) may be positioned along a central axis of the mitral annulus.

In another embodiment, a longitudinal view of the distal cap, where the left atrium and the left ventricle may be visible, may be used to set depth by positioning the distal cap (which may be bright due to echogenicity) relative to the mitral annulus and/or native leaflets (which may be bright and visible on an echocardiogram). The mitral annulus may be visible by its relative location and the point around which the leaflets are moving. For example, the distal cap can be positioned so as to be longitudinally aligned with the mitral annulus and/or leaflets of the replacement valve. In some cases, the desired relative position of the replacement valve may be calculated based on the size of the leaflets, replacement valve, distal cap and/or other features of the delivery system or anatomical structures. For example, the position of the replacement valve may be calculated based on the size of the distal cap relative to the size of one or more of leaflets, replacement valve and/or other features of the delivery system or anatomical structures.

At different views or angles, the operator or physician of a delivery device with an echogenic nosecone can use the same approaches as otherwise described herein, taking into account the angle in which the imaging device is viewing the delivery device. The echogenic features can be used alone or in combination with radio-opaque features described herein. For example, a radio-opaque wire can be used to provide initial information as to the position of the delivery device, and the echogenic features can then be used to provide depth information for placing the replacement valve centrally within the mitral annulus. In some cases, the radio-opaque marker can be used in conjunction with the echogenic features to provide information for correct placement of the replacement valve.

FIGS. 10A and 10B illustrate an exemplary configuration of the guidewire receiving member 1003 and distal cap 1006 that may be utilized in any of the other embodiments described herein. FIG. 10A shows, in cross-section, an embodiment of a distal cap 1006 with an insert 1009 embedded within an outer portion (e.g., a molded portion). In this embodiment, the guidewire receiving member 1003 is comprised of separate sections 1013 and 1015 each joined to the insert 1009. As shown, a proximal section 1013 of the guidewire receiving member 1003 and a distal section 1015 of the guidewire receiving member 1003 are each disposed within the lumen of the elongate member 1010 of the insert 1009. The proximal section 1013 and distal section 1015 may abut each other at a point along any portion of the lumen of the elongate member 1010. Preferably, however, the abutment point is disposed far enough within the lumen to allow for sufficient bonding and/or mechanical fastening of each of the separate sections 1013 and 1015 to the insert 1009.

The distal section 1015 may have relatively greater flexibility (e.g., lower modulus of elasticity) than the proximal section 1013. This beneficially allows the proximal section 1013 to provide greater stiffness and/or columnar strength while the distal section 1015 can provide greater flexibility and better atraumatic properties near the distal tip 1017 of the distal cap 1006. For example, the proximal section 1013 may be formed of a polyimide material (which may optionally include a coiled or braided structure along the entire length of the proximal section 1013 or in one or more discrete sections of the proximal section 1013) and the distal section 1015 may be formed of a material with a lower modulus of elasticity, such as a polyether block amide (e.g., PEBAX®). Other embodiments may include proximal sections and/or distal sections formed from other materials capable of providing a suitable strength and flexibility profile for the guidewire receiving member 1003.

The distal end cap 1006 may be manufactured, for example, by inserting the multi-component guidewire receiving member 1003 into the lumen of the elongate member 1010 and using adhesive bonding to attach the separate sections to the insert 1009 (e.g., using one or more adhesive ports as described above). A mandrel may be utilized to support the guidewire receiving member 1003 during this process, and in particular to support the softer distal section 1015.

The distal end of the distal section 1015 may also be flared. FIG. 10B is an expanded view of the distal end of distal section 1015 (corresponding to the portion shown in circle 1019 of FIG. 10A). The flared end 1021 beneficially minimizes friction and/or binding of the guidewire receiving member 1003 with a guidewire passing therethrough. The flared end 1021 may be aligned with the distal tip 1017 of the distal cap 1006, as shown in FIG. 10A. Alternatively, the flared end 1021 may be extend distally beyond the distal tip 1017 or may terminate proximal of the distal tip 1017.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. An insert for a distal cap of an intravascular delivery device for a prosthetic heart valve, the insert comprising:
    an elongate member comprising a lumen and a port;
    a rim member radially separated from the elongate member, wherein a perimeter of the rim includes a circumferential groove;
    a wall member supporting the rim member, the wall member disposed between the rim member and the elongate member;
    a radiopaque marker received within the circumferential groove, the radiopaque marker being one of: a band, or a ring;
    a guidewire receiving member extending through the lumen of the elongate member and extending both proximally and distally relative to the elongate member;
    wherein the distal cap includes a molded portion configured to fully encase an outer surface of the insert and the radiopaque marker that are embedded within the distal cap.

2. The insert as recited in claim 1, wherein the wall member comprises a plurality of holes.

3. The insert as recited in claim 1, wherein the guidewire receiving member comprises a proximal section and a distal section, and wherein the distal section has greater flexibility than the proximal section.

4. The insert as recited in claim 3, wherein the proximal section and the distal section are separate pieces adjoined to one another within the lumen of the elongate member.

5. The insert as recited in claim 1, wherein the port is defined by a through-hole within at least one wall of the elongate member.

6. The insert as recited in claim 5, wherein the port is positioned in a longitudinally central region of the elongate member and provides access to the lumen, the port being configured to receive glue or adhesive for bonding the insert and the guidewire receiving member.

7. An intravascular device delivery system, the system comprising:
    an elongated member with a proximal end, a distal end, and a longitudinal axis therebetween, the elongated member including:
    a guidewire receiving member extending from the proximal end to the distal end,
    an insert having (i) an elongate member comprising a lumen and a port, (ii) a rim member radially separated from the elongate member, wherein a perimeter of the rim includes a circumferential groove, and (iii) a wall member supporting the rim member, the wall member disposed between the rim member and the elongate member,
    a radiopaque marker received within the circumferential groove, the radiopaque marker being one of: a band, or a ring,
    a distal cap longitudinally fixed to the guidewire receiving member, the distal cap comprising a molded portion that fully encases an outer surface of the insert and the radiopaque marker such that the insert and the radiopaque marker are embedded within the distal cap.

8. The system of claim 7, wherein the insert is adhesively bonded to the guidewire receiving member.

9. The system of claim 8, wherein the insert comprises a plurality of spoke-like members extending between an elongate member of the insert and a rim member of the insert.

10. The system of claim 9, wherein each of the plurality of spoke-like members is tapered.

11. The system of claim 7, wherein the insert comprises a plurality of through-holes extending along a longitudinal axis of the guidewire receiving member.

12. The system of claim 7, wherein the distal cap comprises one or more echogenic features that allow visualization under echocardiography techniques.

13. The system of claim 12, wherein the one or more echogenic features include pores of a porous material or one or more chambers within the distal cap.

14. The system of claim 7, wherein the guidewire receiving member comprises a proximal section and a distal section, and wherein the distal section has greater flexibility than the proximal section.

15. The system of claim 14, wherein the proximal section and the distal section are separate pieces adjoined to one another within the lumen of the elongate member.

16. The system of claim 7, wherein the insert is embedded within the distal cap such that a plane defined by a rim of the insert is substantially perpendicular with respect to a longitudinal axis of the distal cap.

17. The system of claim 7, wherein the guidewire receiving member extends both proximally and distally relative to the elongate member.

18. An intravascular device delivery system, the system comprising:
    an elongated member with a proximal end, a distal end, and a longitudinal axis therebetween, the elongated member including:
    a guidewire receiving member extending from the proximal end to the distal end, and a distal cap longitudinally fixed to the guidewire receiving member, the distal cap comprising an insert mounted to the guidewire receiving member and supporting a radiopaque marker, wherein the guidewire receiving member comprises a proximal section and a distal section, and wherein the distal section has greater flexibility than the proximal section.

* * * * *